United States Patent
Cox

(10) Patent No.: US 8,821,425 B2
(45) Date of Patent: Sep. 2, 2014

(54) DEVICE AND METHOD FOR APPLYING PRESSURE TO MAMMALIAN LIMB

(71) Applicant: Wesley Cox, Fayetteville, AR (US)

(72) Inventor: Wesley Cox, Fayetteville, AR (US)

(*) Notice: Subject to any disclaimer, the term of this patent is extended or adjusted under 35 U.S.C. 154(b) by 0 days.

(21) Appl. No.: 13/731,289

(22) Filed: Dec. 31, 2012

(65) Prior Publication Data
US 2014/0188024 A1 Jul. 3, 2014

(51) Int. Cl.
*A61F 13/10* (2006.01)
*A61F 5/01* (2006.01)

(52) U.S. Cl.
CPC .................................. *A61F 5/01* (2013.01)
USPC ............ 602/20; 602/62; 128/878; 606/201; 606/204

(58) Field of Classification Search
USPC ................ 602/5, 19–21, 23, 26, 60–65, 75; 606/203–204, 201; 128/106.1, 878, 128/882, 892, 95.1, 99.1, 100.1, 112.1, 128/845–846, 881; 2/16, 22, 24, 162; 601/133–138, 143
See application file for complete search history.

(56) References Cited

U.S. PATENT DOCUMENTS

| | | | |
|---|---|---|---|
| 1,473,041 A | 11/1923 | Henderson | |
| 2,211,203 A | 8/1940 | Goldman | |
| 3,075,521 A | 1/1963 | Grassl | |
| 3,696,810 A | 10/1972 | Gaylord, Jr. | |
| D248,872 S | 8/1978 | Thomas | |
| D251,682 S | 4/1979 | Levine | |
| 4,243,028 A * | 1/1981 | Puyana | 602/62 |
| 4,334,528 A | 6/1982 | Gauvry | |
| D265,590 S | 7/1982 | Gauvry | |
| 4,628,918 A | 12/1986 | Johnson, Jr. | |
| 4,966,136 A | 10/1990 | Bates | |
| 5,063,913 A | 11/1991 | Nyi | |
| 5,152,302 A | 10/1992 | Fareed | |
| 5,211,623 A | 5/1993 | Sarkozi | |
| 5,295,949 A | 3/1994 | Hathaway | |
| 5,372,575 A | 12/1994 | Sebastian | |
| 5,445,647 A | 8/1995 | Choy | |
| D369,660 S | 5/1996 | Myoga | |
| 5,921,949 A | 7/1999 | Dray | |
| 6,007,508 A | 12/1999 | Reinhardt et al. | |
| 6,120,472 A | 9/2000 | Singer, Jr. | |
| 6,149,617 A | 11/2000 | McNally | |
| 6,352,074 B1 | 3/2002 | Okada | |
| 6,361,549 B1 | 3/2002 | Asatourian et al. | |
| 6,398,749 B1 | 6/2002 | Slautterback | |
| 6,402,712 B1 * | 6/2002 | Gauvry | 602/26 |
| D462,772 S | 9/2002 | Lamping et al. | |
| 6,485,448 B2 | 11/2002 | Lamping et al. | |
| D488,523 S | 4/2004 | Hamlin | |
| 6,755,800 B2 | 6/2004 | Weaver, II et al. | |
| D500,137 S | 12/2004 | Hely | |
| 6,852,088 B2 | 2/2005 | Gaylord | |
| 7,637,883 B2 | 12/2009 | Nyi | |

(Continued)

*Primary Examiner* — Patricia Bianco
*Assistant Examiner* — Kari Petrik
(74) *Attorney, Agent, or Firm* — Kutak Rock LLP; Bryan P. Stanley

(57) ABSTRACT

A therapeutic pressure strap for applying pressure across a muscle or muscle groups on a mammalian limb is described. The strap is particularly well suited for treating "tennis elbow". The strap contains an adjustable fastening means for securing and tightening the strap around a limb. The strap also possesses a plurality of pressure members (e.g., elongated rubber tubes) that apply separate and discrete areas or points of pressure in a line across a muscle or muscle group and generally perpendicular to the longitudinal axis of the limb.

18 Claims, 2 Drawing Sheets

(56) References Cited

U.S. PATENT DOCUMENTS

| | | |
|---|---|---|
| 7,740,645 B2 | 6/2010 | Babaev |
| 7,951,104 B2 | 5/2011 | Rodgers, Jr. et al. |
| 2002/0169407 A1 | 11/2002 | Glinsboeckel |
| 2007/0161932 A1* | 7/2007 | Pick et al. .......... 602/5 |
| 2010/0042031 A1 | 2/2010 | Anglada |
| 2011/0040227 A1* | 2/2011 | Magri .............. 602/62 |

\* cited by examiner

DEVICE AND METHOD FOR APPLYING PRESSURE TO MAMMALIAN LIMB

BACKGROUND OF THE INVENTION

The present invention relates generally to therapeutic devices. More specifically, the invention relates to a therapeutic pressure strap for applying pressure to a mammalian limb. Particularly, the invention relates to a therapeutic pressure strap for applying pressure across muscles near the insertion point of those muscles (i.e., above muscle tendons). Such devices are commonly used to provide pain relief for inflamed and painful muscles, tendons and joint capsules and are especially used for treating lateral epicondylitis, also known as "tennis elbow".

The pathological condition generally known as tennis elbow afflicts many people. In many instances, tennis elbow (and other forms of tendonitis) is caused by overexertion and overuse of a muscle group during exercise, sports or simple repetitive motion. For example, the repeated movement of the human forearm during tennis combined with the repetitive trauma caused by the transfer of forces from the tennis racket to the forearm causes inflammation and pain that radiates from the insertion point of the common extensor tendon on the lateral portion of the forearm near the elbow.

Orthopedists observe that many patients having various forms of tendonitis, and particularly those having tennis elbow, experience pain relief when pressure is applied across the inflamed muscles and tendons. For those patients with tennis elbow this is traditionally accomplished by placing a compressive strap around the forearm just distal to the elbow joint. Such straps are also utilized during use of the arm (e.g., playing tennis or repetitive movement at work) to dampen muscle movement and thereby reduce additional inflammation of the muscles and tendons.

Many variations of such straps are known in the art. U.S. Pat. No. 4,243,028 is an example of such a strap. U.S. Pat. Nos. 5,152,302 and 5,372,575 show alternative designs. These designs, like many others, focus pressure over a single spot or area of the forearm.

However, the mammalian body is a very dynamic system. Treatments, braces, and straps that provide relief for one patient often do not provide relief for another, which is one reason there is such a large number of orthopedic devices on the market for all types of orthopedic conditions. Accordingly, there is a continuing need for new and innovative orthopedic devices to provide treatment and relief to those patients that do not respond to known treatment methods.

SUMMARY OF THE INVENTION

In one aspect, the invention is a therapeutic pressure strap for applying pressure to the muscles of a mammalian limb. The pressure strap comprises an elongated flexible band for encircling a limb. The band has an adjustable cooperative fastening means proximate the ends of the band for adjustably fastening the band about the limb and adjusting the pressure the strap applies to the limb. A plurality of elongated pressure members are attached to the band. The pressure members are separated from each other by a distance and oriented substantially perpendicular to the longitudinal axis of the limb. During use each pressure member creates a discrete line of pressure across the muscles of the limb.

In another aspect, the invention is a method of simultaneously applying a plurality of discrete lines of pressure across the muscles of a limb. The method comprises the steps of encircling a limb with an elongated strap where the strap has an adjustable cooperative fastening means proximate the ends of the strap for adjustably fastening the strap about the limb. The strap also has a plurality of elongated pressure members. The pressure members are separated from each other by a distance and oriented substantially perpendicular to the longitudinal axis of the limb when the strap is in use. The method also includes the step of adjusting the cooperative fastening means to tighten the strap around the limb thereby compressing each pressure member against the limb to create discrete lines of pressure across the muscles of the limb.

A still further aspect of the invention is a method of simultaneously applying a plurality of discrete lines of pressure to the muscles of a limb. The method comprises the steps of placing a plurality of discrete elongated pressure members against a muscle of a limb where the elongated pressure members are substantially perpendicular to the longitudinal axis of the limb. The elongated pressure members are separated from each other by a distance. The pressure members possess a force transfer surface that extends for a distance across the surface of the limb. The method continues by creating a circumferential compressive force around the limb and concentrating a portion of the compressive force applied to the limb at the force transfer surface of the pressure members.

BRIEF DESCRIPTION OF THE DRAWINGS

These and other more detailed and specific features of the present invention are more fully disclosed in the following specification, reference being had to the accompanying drawings, in which.

DETAILED DESCRIPTION OF TIM INVENTION

In the following description, for purposes of explanation, numerous details are set forth, such as device configurations and movements, to provide an understanding of one or more embodiments of the present invention. Furthermore, the following detailed description is of the best presently contemplated mode of carrying out the invention. The description is not intended in a limiting sense, and is made solely for the purpose of illustrating the general principles of the invention. The various features and advantages of the present invention may be more readily understood with reference to the following detailed description taken in conjunction with the accompanying drawings.

While the invention is described with respect to various embodiments thereof, it will be understood by those skilled in the art that various changes in detail may be made therein without departing from the spirit, scope, and teaching of the invention. Accordingly, the invention herein disclosed is limited only as specified in the claims.

Figure 1A:
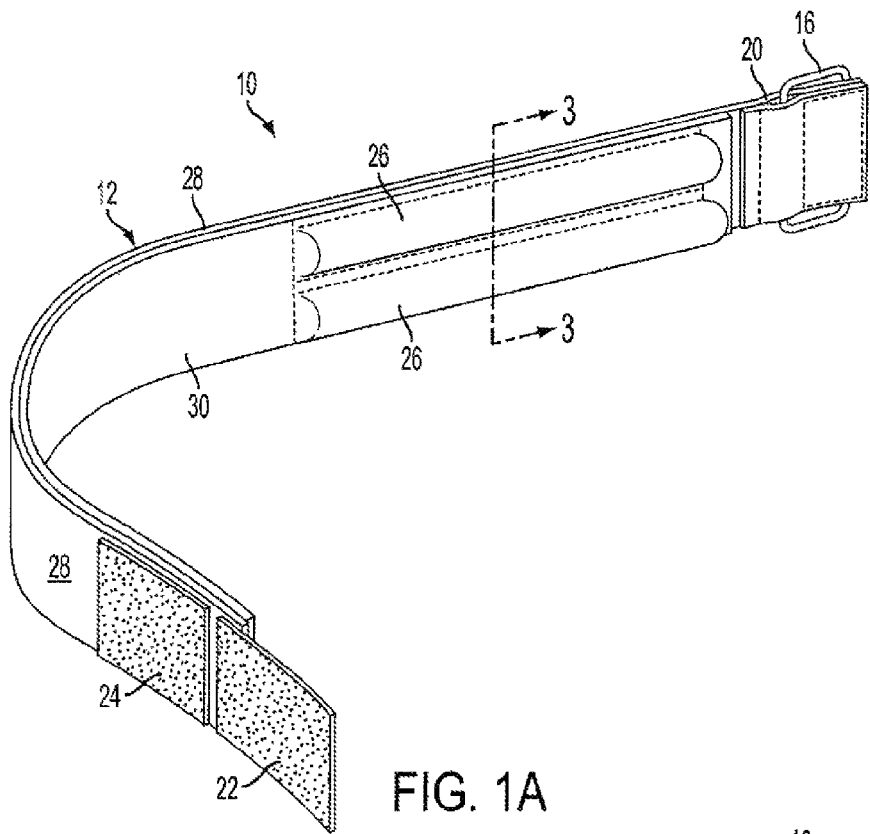
FIG. 1A is a perspective view of an embodiment of the invention.
Figure 1B:
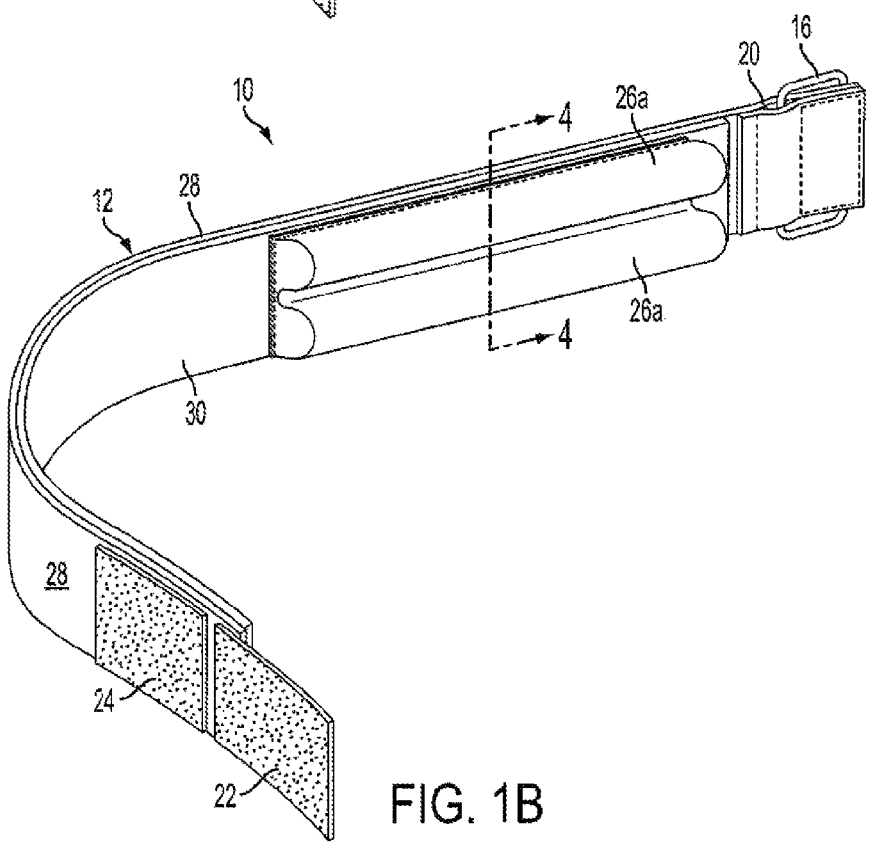
FIG. 1B is a perspective view of an alternative embodiment of the invention.

Referring now to the drawings in detail, where like numerals refer to like parts or elements, there is shown in FIGS. 1A and 1B a therapeutic pressure strap generally designated by the numeral 10. The pressure strap 10 is designed to apply pressure to the muscles of a limb (not shown). For ease of discussion the detailed description describes an embodiment of the invention in the context of a strap used in the treatment of tennis elbow in a human. This narrative convenience should not be interpreted as limiting the scope of the invention.

Broadly speaking, the pressure strap 10 according to the invention comprises an elongated flexible band 12 of sufficient length to encircle the limb to be treated. The pressure strap also comprises an adjustable cooperative fastening means proximate the ends of the band for adjustably fastening the band about the limb, for creating a compressive force or pressure about the limb, and for adjusting the force/pressure applied to the limb. The pressure strap contains a plurality of pockets 26, 26a that are integral with the band 12 where the pockets are separated from each other by a distance 32. An elongated pressure member 34, 34a is contained within each of the pockets. During use of the strap 10, the pressure members 34, 34a are oriented substantially perpendicular to the longitudinal axis of the limb and each pressure member creates a distinct line of pressure across the muscles of the limb. Each element is discussed in more detail below.

The band 12 may be constructed of any suitable flexible material such as woven fabric, vinyl, leather, neoprene, nylon, etc. The material utilized to construct the band may be mostly inelastic or the material can have some elastic qualities. If elastic materials are utilized then care should be taken when the strap is applied to a limb because elastic materials make it easier to inadvertently cut off the circulation to a limb. The flexible band 12 may be made of a single material for ease of manufacture or it can be made from a combination of materials where the materials are chosen for specific purposes. For example, one portion of the band may be made from relatively inelastic leather while another portion is made from somewhat elastic neoprene. In addition, a portion or multiple portions of the band 12 can be formed of solid materials (e.g., thin polymer sheets) to add strength to the strap or focus pressure in a particular area.

The architecture of the band 12 can vary considerably. The band 12 can be made of a single layer of material or it can be made of multiple layers of material. If a single layer of material is used, slight adjustments in the manner of attaching the pressure members 34, 34a (discussed below) to the strap 10 may be necessary. Such adjustments are well within the knowledge of those skilled in the art.

In preferred embodiments the band 12 is formed of multiple layers as shown in FIGS. 1A and 1B. The band 12 shown in the figures comprises a first layer 28 attached to a second layer 30. Additional layers can be utilized if desired. For example a layer of foam could be added to provide comfort for the user.

The therapeutic pressure strap 10 includes an adjustable cooperative fastening means proximate the ends of the ends of the band 12 for adjustably fastening the band about the limb to create a compressive force or pressure about the limb and for adjusting the force/pressure applied to the limb. Suitable cooperative fastening means may include, for example, a metal or polymeric loop 16 attached to the band 12 via a small tube 20 extending across one end of the band and through which the metal loop extends. A Velcro type fastener may be utilized on the opposite end of the band, including a strip of hook portion 22 and a strip of fiber loop portion 24. The fiber loop portion 24 may extend substantially along the length of the band to provide the maximum range of adjustment. Although Velcro type fasteners are preferred due to ease of use, other types of fasteners such as buckles and snaps can be used in the practice of the invention.

Figure 2:
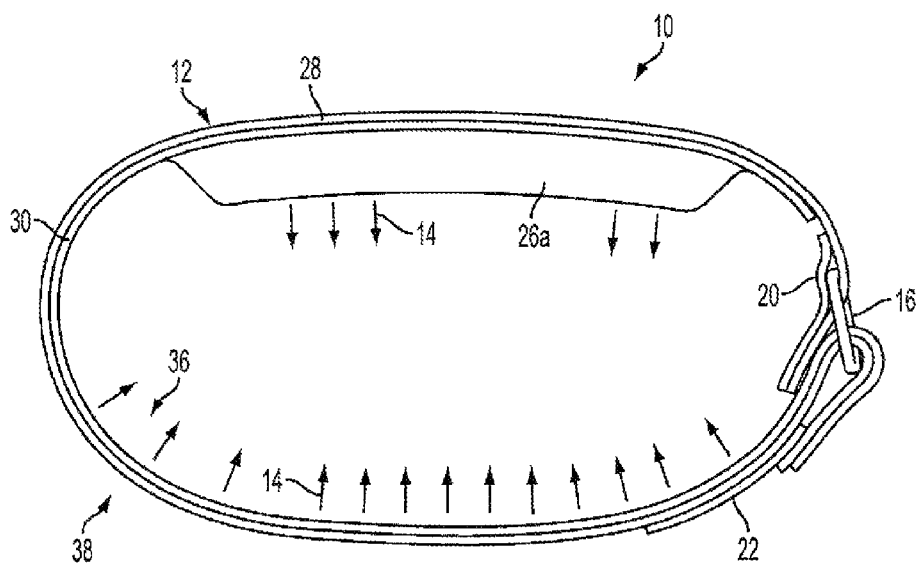
FIG. 2 is a top plan view of the embodiment of FIG. 1B.

FIG. 2 illustrates the engagement of the fastening means and how it can create compressive forces/pressures around a limb. As one end 22 of the strap 10 is pulled through and away from the loop 16 the circumference of the strap 10 contracts causing compressive forces around the interior of the strap. These forces are illustrated by the force vector arrows 14 shown in FIGS. 2, 3 and 4 and are discussed in more detail below.

The strap 10 of the present invention includes means for applying a plurality of discrete lines of pressure to the muscles of a limb. Those skilled in the art recognize that depending upon the placement of the strap, the lines of pressure provided by the strap will be above muscle, or tendon or the transition area between the two. Therefore, as used herein and for clarity, the term muscle or muscles includes the primarily fibrous portions of a muscle, commonly known as tendons, which attach the muscle to bone as well as the contractive tissue commonly referred to as muscle.

In one embodiment of the strap according to the invention the means for applying a plurality of discrete lines of pressure to a limb comprise a plurality of pockets 26, 26a that are integral to a portion of the band 10. The pockets 26, 26a can be formed within the band 12 or formed separately and attached to the band 12.

The manner in which the pockets 26, 26a are formed can vary with the methods used to manufacture the strap. For example, in the embodiment of the invention shown in FIGS. 1A and 3, the strap 10 is formed of multiple layers of material. In this embodiment the strap 10, and more specifically the band 12, is formed of a first layer 28 of material attached to a second layer 30 of material. The method of attaching the first layer 28 to the second layer 30 can be any method known in the art such as sewing or gluing. Those skilled in the art can pick the method of attachment that is most suitable for the materials used to construct the strap 10.

Figure 3:
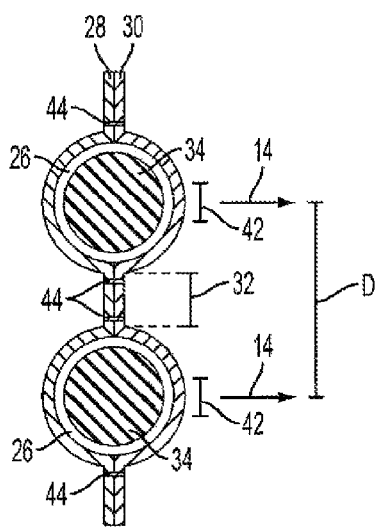
FIG. 3 is a view taken on lines 3-3 of FIG. 1A.

In the embodiment shown in FIG. 3 the first 28 and second 30 layers are joined by sewing the layers together. The pockets 26 are located intermediate the first and second layer in the potential space that exists between the layers. In the embodiment shown in FIG. 3 there exist two pockets 26 formed by two pairs of parallel stitching 44 along the longitudinal axis of the band 12. The pockets 26 can be completely enclosed or they can have small openings (not shown) at one end. Providing small openings allows the user to change out the pressure members (described in more detail below) that reside therein (e.g., remove a more rigid member for a more compliant member).

Figure 4:
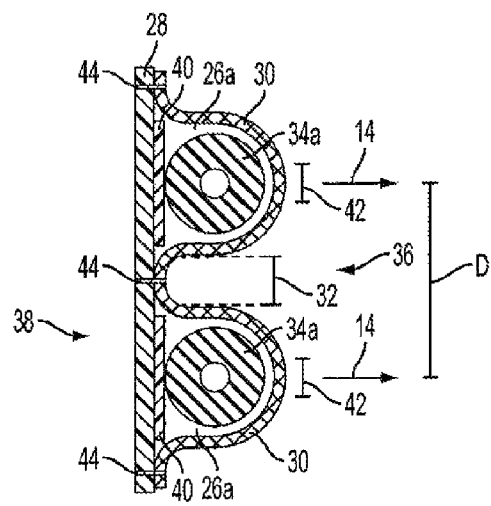
FIG. 4 is a view taken on lines 4-4 of FIG. 1B.

Turning now to FIG. 4, in an alternative embodiment, the pressure strap 10, and more specifically the band 12, is constructed such that the pockets 26a are primarily arranged to be on one side of the strap 10. In both embodiments and particularly the embodiment shown in FIGS. 3 and 4, the pressure strap 10 can be described as having an inside surface 36 and an outside surface 38 where the inside surface 36 faces the limb as shown in FIG. 2. The pockets 26a are positioned primarily on the inside surface 36 of the strap. The pockets 26a in this embodiment can also have small openings (not shown) that allow a user to change out pressure members.

The pockets 26a shown in FIG. 4 are similar to the pockets shown in FIG. 3 in that they are positioned intermediate a first 28 and second 30 layer. They are different in that the portion of the strap 12 that is between pressure members 34a and the outside surface 38 is reinforced to be more rigid and less capable of deforming to conform to the shape of the pressure member 34a as shown in FIG. 4.

The reinforcement of the strap to form the style of pocket 26a shown in FIG. 4 can take several forms. One option is to place a backing plate 40 intermediate the pressure members 34a and the outside surface 38. The backing plate 40 could be semi-flexible (for example, a thin piece of plastic) or made of a rigid material that has a curvature to conform to the natural curvature of the limb. Another alternative for reinforcing the strap is to use multiple layers of material (e.g., fabric, leather) to create the "outer" portion the strap. Either method of reinforcement, results in pockets 26a that generally protrude toward the inside of the strap 10.

The pressure members 34, 34a used in the practice of the invention are sized to fit within the pockets 26, 26a. The pressure members are elongated to provide continuous lines of pressure that extend for a distance across a muscle or muscle group. Those skilled in the art recognize that the pressure (and force vectors) applied by the pressure members 34, 34a to a limb extends along lines that are generally perpendicular to the longitudinal axis of the limb.

Pressure members having a circular or hemispherical cross-section are preferred because they create a generally smooth and uniform force transfer surface (generally represented by numeral 42) when compressed against a limb. Other cross sections (for example, hexagonal or star shaped) can be used in the practice of the invention and may provide more relief for some patients. In addition, the pressure members 34, 34a can be solid or hollow as shown in FIGS. 3 and 4 respectively. Similarly, the material used to construct the pressure members can vary depending upon the amount of pressure desired. For example, a hollow tube of very flexible and soft rubber would have a pressure distribution profile that is different from a solid tube of fairly rigid nylon. One patient may prefer one type of pressure member over another.

In all embodiments of the strap 10, the pockets 26, 26a are separated from each other by a distance 32. The length of the distance 32 is that which is sufficient to create a plurality of separate and discrete lines of pressure across the width of the strap 10. Stated alternatively, the pressure members do not touch or adjoin or abut to create a single, concentrated, uniform area of pressure when the strap is applied to a limb. Stated in yet a further alternative, the lines of force vectors 14 created by the pressure members 34, 34a and which are directed toward the limb are separated by a distance "D" that is greater than the sum of the radii of any two adjacent pressure members 34. Stated more simply, there is a gap between the pressure members 34, 34a.

The distance between the pockets and pressure members can vary depending upon the size of the pressure members, the width of the strap, the pocket material thickness, and the size of the limb. For those straps used in the treatment of tennis elbow, the distance 32 might range between ¼ inch and 1 inch or greater, Furthermore, it is envisioned that the gap distance 32 that provides relief for some patients will not provide relief for other patients. Thus, it is expected that straps 10 of various sizes and gap distances 32 will be manufactured in accordance with the practice of the invention.

Another aspect of the invention is a method of simultaneously applying a plurality of discrete lines of pressure to the muscles of a limb such as a human forearm. The method comprises the step of encircling a limb with an elongated strap such as the strap 10 discussed above. In particular, the strap utilized in the method has an adjustable cooperative fastening means proximate the ends of the strap for adjustably fastening the strap about the limb. The strap also possesses a plurality of elongated pressure members, such as those described previously, where the pressure members are separated by a distance and oriented substantially perpendicular to the longitudinal axis of the limb when the strap is in use. The pressure members are preferably retained within discrete pockets that are integral to the strap as discussed previously.

The method continues by adjusting the cooperative fastening means to tighten the strap around the limb thereby compressing each pressure member against the limb to create discrete lines of pressure across the muscles of the limb where the lines of pressure are separated by a distance.

In yet another aspect, the invention is a method of simultaneously applying a plurality of discrete lines of pressure to the muscles of a limb. The method comprises the step of placing a plurality of discrete elongated pressure members against a muscle of a limb where the elongated pressure members are the same as those discussed in relation to the pressure strap 10 according to the invention. When the strap is in use the elongated pressure members are substantially perpendicular to the longitudinal axis of the limb and are separated from each other by a distance. The pressure members also have a force transfer surface that extends for a distance across the surface of the limb.

The method continues with the step of creating a circumferential compressive force around the limb. This step is typically accomplished by tightening the strap 10 around the limb to create compressive forces similar to those illustrated in FIG. 2. Tightening the strap 10 forces the pressure members, more specifically the force transfer surfaces 42 of the pressure members 34, 34a into the limb, which concentrates a portion of the compressive force applied to the limb at the force transfer surface 42. This in turn creates the continuous lines of pressure that aid in dampening movement of the muscles and tendons.

In the drawings and specification, there have been disclosed typical embodiments on the invention and, although specific terms have been employed, they have been used in a generic and descriptive sense only and not for purposes of limitation, the scope of the invention being set forth in the following claims.

I claim:

1. A therapeutic pressure strap for applying pressure to muscles of a limb, said pressure strap comprising:
   an elongated flexible band for encircling the limb;
   first and second adjustable cooperative fasteners for adjustably fastening said band about the limb, with said first fastener proximate a first end of said band and said second fastener proximate a second end of said band; and
   a plurality of elongated pressure members attached to said band and positioned between said first and second fasteners,
   wherein a longitudinal axis of one or more of said plurality of elongated pressure members is positioned parallel to a longitudinal axis of said band,
   wherein said band includes a plurality of pockets for retaining said pressure members,
   wherein adjacent pockets are separated by stitching along the longitudinal axis of said band, said adjacent pockets being separated by a distance in the range of one quarter inch to one inch,
   wherein said pockets are adapted to be oriented substantially perpendicular to a longitudinal axis of the limb during use whereby pressure members within said pockets are adapted to create discrete lines of pressure across the muscles of the limb.

2. The pressure strap according to claim 1 wherein a portion of said band comprises a first layer attached to a second layer with the pockets being formed by a gap presented between the first and second layer.

3. The pressure strap according to claim 1 wherein said band has an inside surface and an outside surface where the inside surface faces the limb and wherein said plurality of pockets are located on the inside surface of said band.

4. The pressure strap according to claim 3 further comprising a support plate intermediate said inside surface and said outside surface.

5. The pressure strap according to claim 1 wherein the strap is adapted for use with a human forearm.

6. The pressure strap according to claim 1 wherein the lines of the force applied by said pressure members are separated by a distance that is greater than the sum of radii of any two adjacent pressure members.

7. The pressure strap according to claim 6 wherein said elongated pressure members are solid in cross-section.

8. The pressure strap according to claim 6 wherein said elongated pressure members are hollow in cross-section.

9. The pressure strap according to claim 1 wherein a portion of the band is formed of an inelastic material.

10. The pressure strap according to claim 1 wherein a portion of the band is formed of an elastic material.

11. A method of simultaneously applying a plurality of discrete lines of pressure to muscles of a limb, the method comprising the steps of:
    encircling the limb with an elongated strap, said strap having first and second adjustable cooperative fasteners for adjustably fastening said strap about the limb, with said first fastener proximate a first end of said strap and said second fastener proximate a second end of said strap, said strap further having a plurality of elongated pressure members positioned between said first and second fasteners, wherein a longitudinal axis of one or more of said plurality of elongated pressure members is positioned parallel to a longitudinal axis of said strap, wherein said strap includes a plurality of pockets and wherein said pressure members are located in said plurality of pockets, said pockets being oriented substantially perpendicular to a longitudinal axis of the limb during use, and wherein adjacent pockets are separated by stitching along the longitudinal axis of said strap, said adjacent pockets being separated by a distance in the range of one quarter inch to one inch; and
    adjusting the cooperative fasteners to tighten the strap around the limb thereby compressing each pressure member against the limb to create discrete lines of pressure across the muscles of the limb.

12. The method according to claim 11 wherein a portion of said strap comprises a first layer attached to a second layer with the pockets being formed by a gap presented between the first and second layer.

13. The method according to claim 11 wherein said strap has an inside surface and an outside surface wherein the inside surface faces the limb and wherein said plurality of pockets are located on the inside surface of said strap.

14. The method according to claim 11 wherein the limb is a human forearm.

15. The method according to claim 11 wherein each elongated pressure member has a force transfer surface that is rounded and extends for a distance across the surface of a limb.

16. A method of simultaneously applying a plurality of discrete lines of pressure to muscles of a limb, the method comprising the steps of:
    placing a plurality of discrete elongated pressure members against the muscles of the limb, said elongated pressure members being substantially perpendicular to a longitudinal axis of the limb and having a force transfer surface that extends for a distance across a surface of the limb, wherein each of said pressure members is positioned between first and second adjustable cooperative fasteners located on ends of a strap, said pressure members being located in individual pockets of said strap, with adjacent pockets being separated by stitching along a longitudinal axis of said strap, said adjacent pockets being separated by a distance in the range of one quarter inch to one inch, wherein a longitudinal axis of one or more of said plurality of discrete elongated pressure members is positioned parallel to the longitudinal axis of said strap;
    creating a circumferential compressive force around the limb; and
    concentrating a portion of the compressive force applied to the limb at the force transfer surface of said pressure members.

17. The method according to claim 16 wherein the step of creating a circumferential compressive force around the limb comprises tightening the strap around the limb.

18. The method according to claim 17 wherein the pressure members are placed above muscles on a human forearm.

* * * * *